United States Patent
Minomiya et al.

(12)

(10) Patent No.: US 6,235,952 B1
(45) Date of Patent: May 22, 2001

(54) METHOD FOR ISOMERIZING HALOGENATED ETHYLBENZENE AND METHOD FOR SEPARATING HALOGENATED ETHYLBENZENE ISOMERS

(75) Inventors: Eiichi Minomiya; Satoru Miyata, both of Aichi (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/117,620

(22) PCT Filed: Dec. 4, 1997

(86) PCT No.: PCT/JP97/04446

§ 371 Date: Dec. 4, 1998

§ 102(e) Date: Dec. 4, 1998

(87) PCT Pub. No.: WO98/24745

PCT Pub. Date: Jun. 11, 1998

(30) Foreign Application Priority Data

Dec. 5, 1996 (JP) .................................................. 8-325735
May 16, 1997 (JP) .................................................. 9-126622

(51) Int. Cl.[7] .................................................. C07C 17/00
(52) U.S. Cl. .......................................... 570/202; 570/211
(58) Field of Search ...................................... 570/202, 211

(56) References Cited

U.S. PATENT DOCUMENTS

| 4,774,371 | * | 9/1988 | Miwa et al. | 570/211 |
| 5,466,881 | * | 11/1995 | Pies et al. | 570/202 |

FOREIGN PATENT DOCUMENTS

| 0 278 729 A1 | 8/1988 | (EP) . | |
| 0 699 650 A1 | 3/1996 | (EP) . | |
| 5791933 | * 8/1982 | (JP) | 570/202 |
| 08309197 | * 11/1996 | (JP) | 570/202 |
| 09 220474 | 8/1997 | (JP) . | |

* cited by examiner

Primary Examiner—Alan Siegel
(74) Attorney, Agent, or Firm—Austin R. Miller

(57) ABSTRACT

A method for isomerizing a halogenated ethylbenzene characterized by bringing the same into contact with an acidic zeolite containing at least one metal selected among metals of Groups 7 to 11; and a method of efficiently isolating a m-halogenated ethylbenzene from a mixture of halogenated ethylbenzene isomers by adsorption using a specific zeolite X or Y as the adsorbent. The isomerization method enables a halogenated ethylbenzene to be efficiently isomerized with the zeolite catalyst. The separation method enables m-chloroethylbenzene to be efficiently separated from a mixture of chloroethylbenzene isomers by using a specific zeolite as the adsorbent.

13 Claims, 1 Drawing Sheet

METHOD FOR ISOMERIZING HALOGENATED ETHYLBENZENE AND METHOD FOR SEPARATING HALOGENATED ETHYLBENZENE ISOMERS

This application is a 371 of PCT/JP97/04446 filed Dec. 4, 1997.

A method for isomerizing a halogenated ethylbenzene and a method for separating halogenated ethylbenzene isomers.

TECHNICAL FIELD

The present invention relates to a method for isomerizing a halogenated ethylbenzene and a method for separating halogenated ethylbenzene isomers. In more detail, the present invention relates to a method for isomerizing a halogenated ethylbenzene by bringing the same into contact with an acidic zeolite, for obtaining a desired isomer, and a method for separating and recovering a m-halogenated ethylbenzene from a mixture of halogenated ethylbenzene isomers.

BACKGROUND ARTS

Halogenated ethylbenzenes are known as important intermediate products of agricultural chemicals, etc. Especially m-chloroethylbenzene (hereinafter chloroethylbenzene is abbreviated as CEB) or m-bromoethylbenzene (hereinafter bromoethylbenzene is abbreviated as BEB) is expected as a raw material of agricultural chemicals with specific bioactivity as an isomer different from p- and o-isomers.- CEB or BEB is mainly produced by aromatic ring chlorination or bromination reaction of ethylbenzene, but since the reaction is very strong in ortho-orientation and para-orientation, the m-isomer can be produced only in a small amount.

Therefore, CEB and BEB isomerization methods have an important technical significance. Conventionally known isomerization reactions for these compounds include a method of using aluminum chloride, etc. as a catalyst disclosed in Olah. G. A. J. Org. CHEM. 27, 3464 (1962), a method of using $HF—BF_3$ as a catalyst disclosed in Japanese Patent Laid-Open (Kokai) 46-11809, etc. Furthermore, Idar A. Acta Chemica Scandinavica B39,437 (1985) describes a chloroethylbenzene isomerization reaction using a mordenite-type zeolite. Furthermore, methods for isomerizing a halogenated toluene using a zeolite as a catalyst are disclosed in Japanese Patent Laid-Open (Kokai) Nos. 57-40428, 85330, 163327 and 7-309792.

However, in the isomerization reactions of halogenated ethylbenzenes, it has been difficult to efficiently isomerize using conventional catalysts such as aluminum chloride and $HF—BF_3$ since the disproportionation reaction accompanying the de-ethylation reaction or intermolecular migration of ethyl groups is likely to occur, unlike the isomerization reactions of halogenated toluenes. Furthermore, because of such problems as the enormous use of catalyst for isomerization, corrosion of reactor and environmental issue in the treatment of waste catalyst, the conventional methods are not efficient. The isomerization reaction using a mordenite catalyst is less in these problems, but has such a disadvantage that since the catalyst life is short, the zeolite must be regenerated after hundreds of hours. So, a method for more efficiently obtaining a desired halogenated ethylbenzene is strongly demanded.

For separation of halogenated ethylbenzene isomers, since the halogenated ethylbenzene isomers are not so different in boiling point, a precision distillation column with a very large number of stages is necessary for separating them. So, it has been difficult to efficiently separate a m-halogenated ethylbenzene at high purity.

As methods for separating the isomers of chlorotoluene structurally different from halogenated ethylbenzenes of the present invention, Japanese Patent Publication (Tokko) No. 37-5155 discloses an adsorption separation method using a zeolite X as the adsorbent, and Japanese Patent Laid-Open (Kokai) Nos. 57-31627, 35528 and 91933 disclose adsorption separation methods using a K ion exchanged zeolite Y as the adsorbent. These methods can separate the m-isomer from the p-isomer by adsorption, but cannot separate the m-isomer from the o-isomer, and m-chlorotoluene cannot be singly separated as an extract component or raffinate component. Furthermore, Japanese Patent Laid-Open (Kokai) Nos. 58-131923 and 59-176223 disclose m-chlorotoluene separation methods using an Ag and K ion exchanged zeolite Y or a Na and Cu ion exchanged zeolite Y as the adsorbent, and these methods can separate m-chlorotoluene as a raffinate component. However, as far as the inventors examined, these adsorbents could little separate m-CEB. As described so far, no method for adsorbing and separating a halogenated ethylbenzene has been known at all, and there has been no idea of attempting it at all.

DISCLOSURE OF THE INVENTION

The inventors studied intensively to solve the problem, and as a result, found that a halogenated ethylbenzene can be isomerized by bringing the same into contact with an acidic zeolite containing at least one metal selected among metals of Groups 7 to 11. Thus, the present invention has been completed.

The present invention relates to a method of isomerizing a halogenated ethylbenzene, comprising the step of bringing the halogenated ethylbenzene into contact with an acidic zeolite containing at least one metal selected among the metals of Groups 7 to 11 for isomerizing it. In the present invention, it is preferable that the isomerization method is effected in the presence of hydrogen, and that the acidic zeolite is a faujasite-type, beta-type, mordenite-type or pentasil-type zeolite. Furthermore, it is preferable that the halogen of the halogenated ethylbenzene is chlorine or bromine.

On the other hand, the inventors studied intensively on the method for efficiently separating a halogenated ethylbenzene, and found that m-isomer can be efficiently separated from a mixture of halogenated ethylbenzene isomers, particularly of CEB or BEB, by adsorption separation, using an adsorbent containing a specific zeolite and a desorbent. Thus, the present invention as a method for separating halogenated ethylbenzene isomers has been completed. The present invention relates to a method for separating halogenated ethylbenzene isomers, comprising the step of separating a m-halogenated ethylbenzene from a mixture of halogenated ethylbenzene isomers using an adsorbent containing a zeolite X containing an alkali metal and/or alkaline earth metal, or an adsorbent containing a zeolite Y containing sodium, and a desorbent.

In the present invention, the following two embodiments are preferable: a method for separating halogenated ethylbenzene isomers, comprising the step of separating a m-halogenated ethylbenzene as an extract component using an adsorbent containing a zeolite X containing alkali metal cations and not containing silver cations or containing silver cations by less than 10% of the ion exchange sites, or containing a zeolite Y containing sodium, and a method for separating halogenated ethylbenzene isomers, comprising the step of separating a m-halogenated ethylbenzene as a raffinate component using an adsorbent containing a zeolite X containing alkali metal and/or alkaline earth metal cations and containing silver cations by 10% or more of the ion exchange sites.

The present invention is especially effective when the mixture of halogenated ethylbenzene isomers is a mixture of chloroethylbenzene isomers or a mixture of bromoethylbenzene isomers.

Furthermore, in the present invention, it is preferable that the desorbent used is an alkyl substituted aromatic hydrocarbon, halogenated aromatic hydrocarbon or halogenated alkyl substituted aromatic hydrocarbon.

THE BEST EMBODIMENTS OF THE INVENTION

The zeolite used in the halogenated ethylbenzene isomerization method of the present invention can be an acidic zeolite, and it is preferable that the acidic zeolite is a faujasite-type, beta-type, mordenite-type or pentasil-type zeolite. A mordenite-type zeolite and pentasil-type zeolite are more preferable. A method for synthesizing a faujasite-type zeolite is disclosed, for example, in Japanese Patent Publication (Tokko) No. 52-15400, etc. Methods for synthesizing a beta-type zeolite are disclosed, for example, in U.S. Pat. No. 3,308,069 and Japanese Patent Publication (Tokko) 7-223989. Methods for synthesizing a mordenite-type zeolite are disclosed, for example, in Japanese Patent Publication (Tokko) No. 47-46677, Japanese Patent Laid-Open (Kokai) No. 55-26529 and Japanese Patent Publication (Tokko) No. 3-31006. Methods for synthesizing a pentasil-type zeolite are disclosed, for example, in U.S. Pat. Nos. 3,702 886 and 4,511,547 and Japanese Patent Publication (Tokko) No. 60-35284.

When any of said zeolites is used for the isomerization method of the present invention, it is usually preferable to use the zeolite as a formed product, though not limited to it. The forming method is not especially limited, and can be, for example, rolling method, extrusion method or compression method, etc. For forming, if necessary, a binder such as alumina sol or clay, etc. can be added. The formed zeolite is usually calcined at 300 to 700° C., to be activated for use as a catalyst.

When any of the zeolites is used for the isomerization method of the present invention, it is used as an acidic zeolite. An acidic zeolite can be obtained, as is well known, by replacing the cations in a zeolite by hydrogen ions or divalent or higher valent cations. It is especially preferable that the cations are replaced by hydrogen ions, since the activity is high.

For replacing the cations in a zeolite by hydrogen ions, usually the zeolite is ion-exchanged directly by an acid aqueous solution, or the metal cations are ion-exchanged by ammonium ions, being followed by burning. If the zeolite contains organic nitrogen-containing ions beforehand, the organic nitrogen-containing cations can be decomposed by burning for conversion into hydrogen ions, to obtain an acidic zeolite.

The halogenated ethylbenzene used in the method for isomerizing a halogenated ethylbenzene of the present invention can have the substituting halogen position at the ortho (o-), meta (m-) or para (p-) position to the ethyl group. It is preferable that the halogen is chlorine or bromine, and two or more may also substitute. The raw material for isomerization of the present invention can be a single isomer or a mixture of isomers.

The halogenated ethylbenzenes which can be used include, for example, o-chloroethylbenzene, m-chloroethylbenzene, p-chloroethylbenzene, o-bromoethylbenzene, m-bromoethylbenzene, p-bromoethylbenzene, 1,3-dichloro-4-ethylbenzene, 1,3-dichloro-5-ethylbenzene, 1-chloro-2,4-diethylbenzene, 1-chloro-3,5-diethylbenzene, etc.

The isomerization reaction of the present invention can be effected by the flow method or batch method. The reaction is effected with heating. The reaction temperature is usually 100 to 500° C., preferably 150 to 400° C. The reaction pressure is not especially limited, and can be set at atmospheric pressure to any desired pressure. The weight hourly space velocity (WHSV) as the raw material supply velocity per catalyst weight in the reaction is usually 0.01 to 50 hr$^{-1}$, preferably 0.1 to 10 hr$^{-1}$.

In the reaction of the present invention, a halogenated benzene and/or benzene can exist as a diluent together with the raw halogenated ethylbenzene. The dilution ratio is usually 1/20–20/1 (wt/wt), preferably 1/5–5/1 (wt/wt) as a ratio by weight to the halogenated ethylbenzene.

The reaction of the present invention is effected usually in the presence of hydrogen. The amount of hydrogen supplied is usually 0.01 to 40 mol %, preferably 1 to 25 mol % based on the amount of the halogenated ethylbenzene.

The isomerization catalyst of the present invention must contain at least one metal selected from the metals of Groups 7 to 11. The metals which can be used here include silver and copper of Group 11, rhenium of Group 7 and iron, nickel, platinum, etc. of Groups 8 to 10. Especially preferable is silver or rhenium. Methods for introducing the metal include impregnation method, ion exchange method, kneading method, etc. The metal supply sources which can be used include hydrochlorides, nitrates, oxides, etc. The amount of the metal introduced is 0.01 wt % to 5.0 wt % as metal atoms based on the total amount of the catalyst in every case. A preferable range is 0.01 wt % to 1.0 wt %.

The presence of the diluent and hydrogen and the introduction of a metal into the catalyst are effective for preventing the loss of the halogenated ethylbenzene by side reactions such as disproportionation reaction and the degradation of catalyst activity.

The method for separating halogenated ethylbenzene isomers of the present invention is described below in detail.

The zeolite X or Y used in the method for separating halogenated ethylbenzene isomers of the present invention is a faujasite-type zeolite which is a crystalline aluminosilicate represented by the following formula:

where M stands for cations, and n stands for their valence. In a faujasite-type zeolite, x is usually in a range of 2 to 6. The faujasite-type zeolite can be classified into a zeolite X with 2 to 3 as x, and a zeolite Y with 3 to 6 as x. y depends on the hydration degree.

In the present invention, a specific zeolite X or a specific zeolite Y can be used. That is, a zeolite X containing an alkali metal and/or alkaline earth metal as cations M or a zeolite Y containing sodium as cations M is used.

The faujasite-type zeolite is usually obtained as a zeolite containing sodium as cations M, and the cations can be replaced by various cations by ion exchange. The cation exchange is usually effected by bringing the zeolite into contact with an aqueous solution of a compound containing the intended cations such as a hydrochloride, nitrate, sulfate, carbonate or hydroxide, etc. The ion exchanged amount can be set as desired by the concentration of the aqueous solution, though depending on the kind of cations. After completion of ion exchange, the zeolite is sufficiently rinsed, to remove the sodium ions, chlorine ions, nitrate ions, etc. dissolved in the aqueous solution due to ion exchange.

When a m-halogenated ethylbenzene is separated as an extract component in the present invention, a zeolite X containing alkali metal cations and not containing silver cations or containing silver cations by less than 10% of the ion exchange sites, and a zeolite Y containing sodium ions are preferable. The alkali metal cations of the zeolite X include Li, Na, K, Cs, etc., and sodium is especially preferable.

When a m-halogenated ethylbenzene is separated as a raffinate component in the present invention, a zeolite X containing alkali metal and/or alkaline earth metal cations and containing silver cations by 10% or more of the ion exchange sites can be preferably used. The alkali metals include Li, Na, K, Cs, etc., and the alkaline earth metals include Mg, Ca, Sr, Ba, etc.

Especially preferable combinations are Ag and Ba, Ag and K, etc. Such a zeolite can be obtained by ion-exchanging the sodium of a faujasite-type zeolite by an alkali metal or alkaline earth metal, and then ion-exchanging 10% to 70% of the sodium cation sites of the zeolite by silver. It is preferable to exchange 10% to 40%. When silver cations are not contained or contained by less than 10%, the m-halogenated ethylbenzene can be separated as an extract component.

The adsorbent can be a solidified zeolite only or can be grains obtained by granulating a zeolite together with a binder such as alumina or clay.

Before the adsorbent is used, the crystal water in the zeolite is removed beforehand. Usually by heating at 200 to 600° C., most of crystal water can be removed.

The adsorption separation technique for adsorbing and separating the CEB isomer mixture or BEB isomer mixture using the adsorbent of the present invention can be the so-called chromatographic fractionation method or an adsorption separation method using a simulated moving bed as a continuous version of said method.

The continuous adsorption separation technique using a pseudo-moving bed is effected by continuously using the following adsorption operation, concentration operation and desorption operation in circulation.

[1] Adsorption operation: The raw materials containing a halogenated ethylbenzene isomer mixture are brought into contact with the adsorbent of the present invention, and the most absorbable component is selectively adsorbed. The most absorbable component is recovered with the desorbent described later, as an extract component.

[2] Concentration operation: The raffinate containing a less absorbable component in a large amount is further brought into contact with the adsorbent, and the most absorbable component is selectively adsorbed, while the less absorbable component in the raffinate becomes highly purified.

[3] Desorption operation: The highly purified less absorbable component is recovered as a raffinate. On the other hand, the most adsorbable component is expelled from the adsorbent by a desorbent, and recovered as an extract component together with the desorbent.

It is preferable that the desorbent used for the above adsorption separation method is an alkyl substituted aromatic hydrocarbon or a halogenated aromatic or halogenated alkyl substituted aromatic hydrocarbon. The alkyl substituted aromatic hydrocarbons which can be used here include, for example, toluene, ethylbenzene, xylene, propylbenzene, trimethylbenzene, diethylbenzene, tetramethylbenzene, etc.

The halogenated aromatic hydrocarbons which can be used here include, for example, chlorobenzene, dichlorobenzene, trichlorobenzene, etc. The halogenated alkyl substituted aromatic hydrocarbons include, for example, chlorotoluene, dichlorotoluene, chloroxylene, etc.

Especially for separation of m-CEB, preferable are p-xylene, 1,2,4-trimethylbenzene, m-chlorotoluene and 3,4-dichlorotoluene. For separation of m-BEB, preferable are p-xylene and 3,4-dichlorotoluene. Any or more as a mixture of these adsorbents can be used.

As operation conditions of the adsorption separation method, the temperature is usually room temperature to 350° C., preferably 50 to 250° C., and the pressure is usually atmospheric pressure to 4 MPa, preferably atmospheric pressure to 3 MPa. The adsorption separation method of the present invention can be effected also in vapor phase, but to decrease the unpreferable side reactions of the raw materials and desorbent by lowering the operation temperature, it is preferable to execute the method in liquid phase.

EXAMPLES

The present invention will be described below in more detail with reference to examples and comparative examples, which are not intended to restrict the scope of the invention.

The synthesis of zeolites, preparation of isomerizing catalysts, adsorption characteristics of adsorbents and preparation of adsorbents respectively used in the following examples and comparative examples are described below.

[Synthesis of Zeolites]

Zeolite 1

A resin beaker was charged with 229.3 g of ion exchange water, and 3.1 g of sodium hydroxide and 14.7 g of sodium aluminate ($Al_2O_3$=18.76 wt %, $Na_2O$=19.71 wt %, $H_2O$=61.53 wt %) were added. The mixture was sufficiently stirred for dissolution. Then, 9.2 g of tartaric acid was added, and the mixture was sufficiently stirred. Furthermore, 48 g of silicic acid powder ($SiO_2$=89.33 wt %, $Na_2O$=0.31 wt %, $Al_2O_3$=0.34 wt %, $H_2O$=10.02 wt %) was added, to prepare a slurry. The slurry was supplied into a 500 cc stainless steel autoclave and reaction was effected with sufficient stirring at 160° C. for 3 days, to produce a zeolite. The zeolite was sufficiently washed by distilled water, and dried at 120° C. overnight, to obtain a pentasil-type zeolite with a $SiO_2$/$Al_2O_3$ molar ratio of 20.

Zeolite 2

A resin beaker was charged with 228.5 g of ion exchange water, and 5.4 g of sodium hydroxide and 35.9 g of sodium aluminate ($Al_2O_3$=18.76 wt %, $Na_2O$=19.71 wt %, $H_2O$=61.53 wt % were added. The mixture was sufficiently stirred for dissolution. Then, 12.5 g of tartaric acid was added, and the mixture was sufficiently stirred. Furthermore, 45.9 g of silicic acid powder($SiO_2$=89.33 wt %, $Na_2O$=0.31 wt %, $Al_2O_3$=0.34 wt %, $H_2O$=10.02 wt %) was added, to prepare a slurry. The slurry was supplied into a 500 cc stainless steel autoclave, and reaction was effected with sufficient stirring at 165° C. for 2 days, to produce a zeolite. The zeolite was sufficiently washed with distilled water and dried at 120° C. overnight, to obtain a mordenite-type zeolite with a $SiO_2/Al_2O_3$ molar ratio of 10.

Zeolite 3

A resin beaker was charged with 220.3 g of ion exchange water, and 19.6 g of sodium hydroxide and 11.3 g of sodium aluminate ($Al_2O_3$=18.76 wt %, $Na_2O$=19.71 wt %, $H_2O$=61.53 wt %) were added. The mixture was sufficiently stirred for dissolution. Then, 9.1 g of tartaric acid was added, and the mixture was sufficiently stirred. Furthermore, 46.3 g of silicic acid powder($SiO_2$=89.33 wt %, $Na_2O$=0.31 wt %, $Al_2O_3$=0.34 wt %, $H_2O$=10.02 wt %) was added, to prepare a slurry. The slurry was supplied into a 500 cc stainless steel autoclave, and reaction was effected with stirring at 155° C. for 2 days, to produce a zeolite. The zeolite was sufficiently washed with distilled water and dried at 120° C. overnight, to obtain a mordenite-type zeolite with a $SiO_2/Al_2O_3$ molar ratio of 20.

Zeolite 4

A resin beaker was charged with 232.6 g of ion exchange water, and 0.67 g of sodium hydroxide was added for sufficient dissolution. Then, 26.9 g of tetraethylammonium hydroxide (content 20 wt %, $H_2O$=80 wt %) was added, and in succession, 10. 2 g of sodium aluminate ($Al_2O_3$=18.76 wt %, $Na_2O$=19.71 wt %, $H_2O$=61.53 wt %) was added. The mixture was sufficiently stirred, and finally 33 g of silicic acid powder($SiO_2$=89.33 wt %, $Na_2O$=0.31 wt %, $Al_2O_3$=0.34 wt %, $H_2O$=10.02 wt %) was added, to prepare a slurry. The slurry was supplied into a 500 cc stainless steel autoclave, and reaction was effected with sufficient stirring at 160° C. for 7 days, to produce a zeolite. The zeolite was sufficiently washed with distilled water and dried at 120° C. overnight, to obtain a mordenite-type zeolite with a $SiO_2/Al_2O_3$ molar ratio of 20.

[Preparation of Catalysts]

Catalyst 1

Alumina sol ($Al_2O_3$=10 wt %) was added by 15 parts by weight as alumina to 100 parts by weight of the zeolite 1, and the mixture was formed, dried at 120° C. overnight and calcined at 500° C. for 2 hours. The formed zeolite was ion-treated using 10 wt % ammonium chloride aqueous solution (solid liquid ratio 2.0 l/kg) at 85° C. for 1 hour five times, sufficiently washed with distilled water, dried at 120° C. overnight and calcined at 550° C. for 2 hours in air, to obtain an acidic pentasil-type zeolite catalyst.

Catalyst 2

An acidic mordenite-type zeolite catalyst was obtained as described to obtain the catalyst 1, except that the zeolite 2 was used and that calcination was effected at 520° C. for 2 hours in air.

Catalyst 3

An acidic mordenite-type zeolite catalyst was obtained as described to obtain the catalyst 1, except that the zeolite 3 was used and that calcination was effected at 520° C. for 2 hours in air.

Catalyst 4

Alumina sol ($Al_2O_3$=10 wt %) was added by 15 parts by weight as alumina to 100 parts by weight of the zeolite 4, and the mixture was formed, dried at 120° C. overnight and calcined at 500° C. for 2 hours. The formed zeolite was ion-treated using 10 wt % ammonium chloride aqueous solution (solid liquid ratio 2.0 l/kg) at 85° C. for 1 hour five times and sufficiently washed with distilled water. The formed zeolite was immersed in a rhenium peroxide ($Re_2O_7$) aqueous solution with a solid liquid ratio of 2.0 l/kg adjusted to be 0.1 wt % as rhenium metal content, at room temperature for 4 hours, filtered, dried at 120° C. overnight, and calcined at 550° C. for 2 hours in air, to obtain a rhenium carried acidic mordenite-type zeolite catalyst.

Catalyst 5

Alumina sol ($Al_2O_3$=10 wt %) was added by 15 parts by weight as alumina to 100 parts by weight of the zeolite 4, and the mixture was formed, dried at 120° C. overnight and calcined at 500° C. for 2 hours. The formed zeolite was ion-treated using 10 wt % ammonium chloride aqueous solution (solid liquid ratio 2.0 l/kg) at 85° C. for 1 hour five times, sufficiently washed with distilled water, dried at 120° C. overnight and calcined at 550° C. for 2 hours in air, to obtain an acidic mordenite-type zeolite.

[Adsorption Characteristics of Adsorbents]

In the examples, the adsorption characteristic of an adsorbent was expressed by the adsorption selectivity ($\alpha$) of the following formula (1):

$$\alpha(o/m \text{ or } p/m) = \frac{\dfrac{\text{Weight percent of } o \text{ or } p}{\text{Weight percent of } m}}{\dfrac{\text{Weight percent of } o \text{ or } p}{\text{Weight percent of } m}} \qquad (1)$$

where o, m or p stands for o-, m- or p-halogenated ethylbenzene respectively; A stands for adsorption phase; and U stands for liquid phase balanced with adsorption phase.

If the $\alpha$ value in the above formula is larger than 1, the m-halogenated ethylbenzene is less likely to be adsorbed than the o- and p-halogenated ethylbenzenes, and if smaller than 1, the m-halogenated ethylbenzene is more likely to be adsorbed than the o- and p-halogenated ethylbenzenes. The adsorbent suitable for separating and recovering the m-halogenated ethylbenzene is preferably larger than 1 or smaller than 1, being close to 0 in both $\alpha$ (o/m) and $\alpha$ (p/m).

[Preparation of Adsorbents]

The adsorbents 1 to 5 used in the examples were prepared according to the following methods:

Adsorbent 1

Alumina sol (Nissan Chemical No. 200: $Al_2O_3$=10 wt %) as a binder was added by 15 parts by weight as alumina to 100 parts by weight a sodium type zeolite X (hereinafter expressed as NaX) (Zeolam F-9 powder produced by Tosoh Corp.), and the mixture was granulated to 0.15–0.5 mm dia., to obtain a NaX type zeolite. It was dried at 120° C. and calcined at 500° C.

Adsorbent 2

Alumina sol (Nissan Chemical No. 200: $Al_2O_3$=10 wt %) as a binder was added by 15 parts by weight as alumina to 100 parts by weight of a sodium type zeolite Y (hereinafter expressed as NaY) (Zeolam Na-5.1Y powder produced by Tosoh Corp.), and the mixture was granulated to 0.15–0.5 mm dia., to obtain a NaY type zeolite. It was dried at 120° C. and calcined at 500° C.

Adsorbent 3: Ag—BaX

The adsorbent 1 was treated for ion exchange using 10 wt % barium nitrate aqueous solution (solid liquid ratio 3.0 l/kg) at 85° C. for 1 hour six times and sufficiently washed with distilled water. Then, using a silver nitrate aqueous solution (solid liquid ratio 3.0 l/kg) as silver corresponding to 40% of the Na cation sites of NaX, it was allowed to stand at room temperature for 30 minutes and treated for ion exchange at 85° C. for 1 hour, sufficiently washed with distilled water, dried at 120° C. and calcined at 500° C.

Adsorbent 4: Ag—NaX

Using a silver nitrate aqueous solution (solid liquid ratio 3.0 l/kg) as silver corresponding to 5% of the Na cation sites of NaX, the adsorbent 1 was allowed to stand at room temperature for 30 minutes and treated for ion exchange at 85° C. for 1 hour, sufficiently washed with distilled water, dried at 120° C. and calcined at 500° C.

Adsorbent 5: Ag—KY

Using 10 wt % potassium nitrate aqueous solution (solid liquid ratio 3.0 l/kg), the adsorbent 2 was treated for ion exchange at 85° C. for 1 hour ten times, and sufficiently washed with distilled water. Then, using a silver nitrate aqueous solution (solid liquid ratio 3.0 l/kg) as silver corresponding to 30% of the Na cation sites of NaY, it was allowed to stand at room temperature for 30 minutes and treated for ion exchange at 85° C. for 1 hour, sufficiently washed with distilled water, dried at 120° C. and calcined at 500° C.

[Isomerization Reaction]

Examples and comparative examples of isomerization reaction are described below.

Example 1

A 10 ml stainless steel autoclave was charged with 3 g of a mixture consisting of o-chloroethylbenzene (CEB) and chlorobenzene (CB) (o-CEB/CB=2 (wt/wt)), and 0.5 g of the catalyst 1 was added to it. At room temperature and atmospheric pressure, 20 ml of hydrogen was supplied, and reaction was effected at 250° C. for 2 hours. The amount of hydrogen supplied corresponded to 5.6 mol % based on the amount of o-CEB. After completion of reaction, the reaction product was analyzed by gas chromatography. The results are shown in Table 1.

Example 2

Reaction was effected as described in Example 1, except that p-CEB was used instead of o-CEB. The results are shown in Table 1.

Example 3

A 10 ml stainless steel autoclave was charged with 2 g of a CEB isomer mixture (o-:m-:p-=52.0:0.6:47.4 (wt %)), and 0.5 g of the catalyst 1 was added. At room temperature and at atmospheric pressure, 20 ml of hydrogen was supplied, and reaction was effected at 250° C. for 4 hours. The amount of hydrogen supplied corresponded to 5.6 mol % based on the amount of the CEB isomer mixture. After completion of reaction, the reaction product was analyzed by gas chromatography. The results are shown in Table 1.

Example 4

Reaction was effected as described in Example 3, except that 3 g of a mixture consisting of the CEB isomer mixture used in Example 3 and benzene (Bz) (CEB/Bz=2 (wt/wt)) was used. The results are shown in Table 1.

Example 5

Reaction was effected as described in Example 3, except that 3 g of a mixture consisting of the CEB isomer mixture used in Example 3 and CB (CEB/CB=2 (wt/wt)) was used. The results are shown in Table 1.

TABLE 1

| Example | Raw material | CEB composition, % | | |
|---|---|---|---|---|
| | | o- | m- | p- |
| 1 | o-CEB/CB = 2 (wt/wt) | 82.0 | 12.9 | 5.1 |
| 2 | p-CEB/CB = 2 (wt/wt) | 4.7 | 59.6 | 35.6 |
| 3 | CEB | 52.4 | 19.7 | 27.9 |
| 4 | CEB/Bz = 2 (wt/wt) | 51.9 | 26.5 | 21.6 |
| 5 | CEB/CB = 2 (wt/wt) | 51.8 | 24.3 | 23.9 |

Example 6

A 10 ml stainless steel autoclave was charged with 3 g of a mixture consisting of a CEB isomer mixture (o-: m-: p-=65.0:2.7:32.3 (wt %)) and CB (CEB/CB=2 (wt/wt)), and 0.5 of the catalyst 2 was added to it. At room temperature and atmospheric pressure, 20 ml of hydrogen was supplied, and reaction was effected at 270° C. for 2 hours. The amount of hydrogen supplied corresponded to 5.6 mol % based on the amount of the CEB isomer mixture. After completion of reaction, the reaction product was analyzed by gas chromatography. The results are shown in Table 2.

Example 7

Reaction was effected as described in Example 6, except that the catalyst 3 was used. The results are shown in Table

TABLE 2

| Example | Catalyst | CEB composition, % | | |
|---|---|---|---|---|
| | | o- | m- | p- |
| 6 | Catalyst 2 | 64.4 | 4.2 | 31.4 |
| 7 | Catalyst 3 | 56.4 | 19.6 | 24.00 |

Example 8

A 10 ml stainless steel autoclave was charged with 2 g of a CEB isomer mixture (o-:m-:p-=49.2:2.7:48.1 (wt %)), and 1.0 g of the catalyst 4 was added. At room temperature and atmospheric pressure, 20 ml of hydrogen was supplied, and reaction was effected at 270° C. for 2 hours. The amount of hydrogen supplied corresponded to 5.6 mol % of the CEB isomer mixture. After completion of reaction, the reaction product was analyzed by gas chromatography. The results are shown in Table 3.

Example 9

Reaction was effected as described in Example 8, except that 2.5 g of a mixture consisting of the CEB isomer mixture used in Example 8 and CB (CEB/CB=4 (wt/wt)) was used. The results are shown in Table 3.

Example 10

Reaction was effected as described in Example 8, except that 3 g of a mixture consisting of the CEB isomer mixture used in Example 8 and CB (CEB/CB=2 (wt/wt)) was used. The results are shown in Table 3.

TABLE 3

| Example | Raw material | CEB composition, % | | |
|---|---|---|---|---|
| | | o- | m- | p- |
| 8 | CEB | 29.8 | 49.4 | 20.7 |
| 9 | CEB/CB = 4 | 31.5 | 47.2 | 21.3 |
| 10 | CEB/CB = 2 | 32.6 | 45.8 | 21.6 |

Example 11

A fixed bed flow reactor was used for isomerization reaction using the catalyst 1, by supplying hydrogen to a mixture consisting of a CEB isomer mixture (o-:m-:p-=59.0:5.6:35.4 (wt %)) and CB (CEB/CB2 (wt/wt)) by 5.6 mol % based on the amount of the CEB isomer mixture. The results are shown in Table 4.

Example 12

Reaction was effected as described in Example 11, except that the catalyst 3 was used. The results are shown in Table 4.

TABLE 4

| Example | Catalyst | CEB recovery rate, % with m-CEB/CEB = 45 wt % |
|---|---|---|
| 11 | Catalyst 1 | 84.3 |
| 12 | Catalyst 3 | 98.5 |

Reaction conditions: WHSV (CEB)=1.3 hr$^{-1}$, reaction temperature 280° C. reaction pressure 4 MPa

Example 13

Reaction was effected using a fixed bed flow reactor and a CEB isomer mixture (o-:m-:p-=59.0:5.6:35.4 (wt %)) as described in Example 11, except that the catalyst 4 was used. The results are shown in Table 5.

Example 14

Reaction was effected as described in Example 11, except that the catalyst 4 was used and that a mixture consisting of a CEB isomer mixture (o-:m-:p-=59.0:5.6:35.4 (wt %)) and CB (CEB/CB=2 (wt/wt)) was used. The results are shown in Table 5.

Comparative Example 1

Reaction was effected using the catalyst 4 as described in Example 14, except that hydrogen was not supplied. The results are shown in Table 5. It can be seen that if no hydrogen exists, the catalyst activity declines 6% about 200 hours later.

Comparative Example 2

Reaction was effected as described in Example 13, except that the catalyst 5 was used. The results are shown in Table 5. It can be seen that an acidic mordenite-type zeolite catalyst without containing any metal declines very greatly in catalyst activity even if hydrogen exists.

TABLE 5

| Example | m-CEB composition, % Reaction time, hr | | | CEB recovery rate, % with |
|---|---|---|---|---|
| | 10 | 100 | 200 | m-CEB/CEB = 48 wt % |
| 13 | 48.7 | 48.5 | 48.2 | 97.0 |
| 14 | 50.1 | 49.7 | 49.4 | 99.0 |
| Comparative Example | | | | |
| 1 | 48.6 | 45.4 | 42.6 | 99.0 |
| 2 | 50.3 | 45.3 | 43.1 | 96.0 |

Reaction conditions: WHSV (CEB)=1.3 hr$^{-1}$, reaction temperature 245° C., reaction pressure 4 MPa.

[Adsorption separation]

Examples and comparative examples of adsorption separation are described below.

Example 15–Example 22

The adsorption selectivities between respective CEB isomers were measured using the adsorbent 1 and various desorbents.

For measurement, a 5 ml autoclave was charged with 3 g of a liquid phase mixture and 1.5 g of the adsorbent calcined at 500° C., and the mixture was allowed to stand at 130° C. for 1 hour with stirring sometimes. The composition of the supplied liquid phase mixture was n-nonane:desorbent:CEB (o:m:p=37%:44%:19%)=8%:60%:32%. The n-nonane was added as an internal standard substance for gas chromatography, which was substantially inactive in adsorption under the above experimental conditions.

The composition of the liquid phase mixture after contact with the adsorbent was analyzed by gas chromatography, and adsorption selectivities between respective CEB isomers were obtained using the formula (1). The results are shown in Table 6.

TABLE 6

| Example | Desorbent | ap/m | ao/m |
|---|---|---|---|
| 15 | p-xylene | 0.21 | 0.46 |
| 16 | iso-propylbenzene | 0.41 | 0.71 |
| 17 | 1,2,4-trimethylbenzene | 0.43 | 0.46 |
| 18 | 1,2,3,5-tetramethylbenzene | 0.48 | 0.78 |
| 19 | o-chlorotoluene | 0.39 | 0.76 |
| 20 | 3,4-dichlorotoluene | 0.48 | 0.78 |
| 21 | 1,2,4-trichlorobenzene | 0.40 | 0.79 |

Example 22 and Example 23

Experiments were performed as described in Example 15, except that the adsorbent 2 was used. In Example 22, o-xylene was used as the desorbent, and in Example 23, 1,2,4-trimethylbenzene was used as the desorbent. The results are shown Table 7.

TABLE 4

| Example | Desorbent | ap/m | ao/m |
|---|---|---|---|
| 22 | o-xylene | 0.20 | 0.54 |
| 23 | 1,2,4-trimethylbenzene | 0.30 | 0.54 |

Example 24–Example 26

Experiments ere performed as described in Example 15, except that the adsorbent 3 was used. In Example 24, o-xylene was as the desorbent, and in Example 25, m-chlorotoluene was the desorbent. In Example 26, 3,4-dichlorotoluene was the desorbent. The results are shown in Table 8.

TABLE 5

| Example | Desorbent | ap/m | ao/m |
| --- | --- | --- | --- |
| 24 | o-xylene | 1.38 | 1.28 |
| 25 | m-chlorotoluene | 2.54 | 1.11 |
| 26 | 3,4-dichlorotoluene | 2.08 | 1.29 |

Example 27

An experiment was performed as described in Example 15, except that the adsorbent 4 was used and that 3,4-dichlorotoluene was used as the desorbent. The results are shown Table 9.

TABLE 9

| Example | Desorbent | ap/m | ao/m |
| --- | --- | --- | --- |
| 13 | 3,4-dichlorotoluene | 0.45 | 0.88 |

Example 28

The adsorption selectivities between respective BEB isomers were measured using the adsorbent 1. The measuring method was as described in Example 15. The composition of the supplied liquid phase mixture was n-nonane:desorbent:BEB (o:m:p=34% :40%:26%)= 13%:46%:41%. The results are shown in Table 7.

TABLE 10

| Example | Adsorbent | ap/m | ao/m |
| --- | --- | --- | --- |
| 28 | p-xylene | 0.24 | 0.44 |

Example 29

Adsorption selectivities between respective BEB isomers were measured using the adsorbent 3, as described in Example 15. As the desorbent, 3,4-dichlorotoluene was used. The composition of the supplied liquid phase mixture was n-nonane:desorbent:BEB (o:m:p=34%.:40%:26%)= 13%:46%:41%. The results are shown in Table 11.

TABLE 11

| Example | Desorbent | ap/m | ao/m |
| --- | --- | --- | --- |
| 29 | 3,4-dichlorotoluene | 2.23 | 1.13 |

Comparative Example 3

An experiment was performed as described in Example 15, except that the adsorbent 1 was used and that xylene was used as the desorbent. The adsorption characteristics of chlorotoluene and CEB were compared, and the results are shown in Table 12.

TABLE 12

(Comparative Example)

| Adsorbent | Chlorotoluene | | CEB | |
| --- | --- | --- | --- | --- |
| | ap/m | ao/m | ap/m | ao/m |
| p-xylene | 0.68 | 0.97 | 0.21 | 0.46 |

Comparative Example 4

An experiment was performed as described in Example 15, except that the adsorbent 5 was used and that 3,4-dichlorotoluene was used as the desorbent. The adsorption characteristics of chlorotoluene and CEB were compared, and the results are shown in Table 13.

TABLE 13

(Comparative Example)

| Desorbent | Chlorotoluene | | CEB | |
| --- | --- | --- | --- | --- |
| | ap/m | ao/m | ap/m | ao/m |
| 3,4-dichlorotoluene | 1.41 | 1.40 | 1.68 | 1.09 |

Example 30

A 1 m long 4.75 mm inner dia. stainless steel column was packed with the adsorbent 1, and p-xylene as a desorbent was fed at a flow rate of about 1.8 ml/min in a 130° C. oil bath. While para-xylene was fed, about 1.6 ml of an isomer mixture consisting of CEB (o:m:p=37%:44%:19%):n-nonane=4:1 (ratio by weight) was introduced into the inlet of the column, as a raw material to be separated. The n-nonane was used as a reference for elution time, and its adsorption is virtually negligible compared with other components. The eluate from the outlet of the column was analyzed by gas chromatography, and elution curves shown in FIG. 1 were obtained.

INDUSTRIAL APPLICABILITY

As described above, according to the present invention, a halogenated ethylbenzene can be isomerized by bringing the same into contact with a zeolite, for effectively obtaining a desired halogenated ethylbenzene. Furthermore, according to the present invention, by an adsorption separation method using a specific zeolite X or Y as the adsorbent, a m-halogenated ethylbenzene can be efficiently obtained from a mixture of halogenated ethylbenzene isomers. Therefore, the present invention is suitable for industrial production of a desired halogenated ethylbenzene, above all, a m-halogenated ethylbenzene.

What is claimed is:

1. A method for isomerizing a halogenated ethylbenzene, comprising the step of bringing said halogenated ethylbenzene into contact with an acidic zeolite containing at least one metal selected from the group consisting of metals of any of Groups 7 to 11, for isomerization.

2. A method for isomerizing a halogenated ethylbenzene, according to claim 1, wherein said isomerization is effected in the presence of hydrogen.

3. A method for isomerizing a halogenated ethylbenzene, according to claim 2, wherein said halogen is chlorine and/or bromine.

4. A method for isomerizing a halogenated ethylbenzene, according to claim 1, wherein said acidic zeolite is selected from the group consisting of faujasite, beta, mordenite and pentasil zeolite.

5. A method for isomerizing a halogenated ethylbenzene, according to claim 1, wherein said contact of said halogenated ethylbenzene with said acidic zeolite, is performed in the presence of a halogenated benzene and/or benzene.

6. A method for isomerizing a halogenated ethylbenzene, according to claim 1, wherein said isomerization reaction is conducted at a temperature of 150 to 400° C.

7. A method for separating a halogenated ethylbenzene isomer, comprising the step of separating a m-halogenated ethylbenzene from a mixture of halogenated ethylbenzenes, by contacting said mixture with an adsorbent containing a zeolite X containing an alkali metal and/or alkaline earth metal, or an adsorbent containing a zeolite Y containing sodium, and a desorbent.

8. A method for separating a halogenated ethylbenzene isomer, according to claim 7, wherein said halogen is chlorine and/or bromine.

9. A method for separating a halogenated ethylbenzene isomer, according to claim 7, wherein an adsorbent containing a zeolite X containing alkali metal cations and free of silver cations or containing silver cations in an amount less than 10% of the ion exchange sites, or an adsorbent containing a zeolite Y containing sodium as the adsorbent, to separate the m-halogenated ethylbenzene as an extract component.

10. A method for separating a halogenated ethylbenzene isomer, according to claim 7, wherein said mixture is contacted with an adsorbent containing a zeolite X containing alkali metal and/or alkaline earth metal cations and containing silver cations in an amount of 10% or more of the ion exchange sites, for separating the m-halogenated ethylbenzene as a raffinate component.

11. A method for separating a halogenated ethylbenzene isomer, according to claim 7, wherein said halogenated ethylbenzene isomer mixture is a chloroethylbenzene isomer mixture.

12. A method for separating a halogenated ethylbenzene isomer, according to claim 7, wherein said desorbent is an alkyl substituted aromatic hydrocarbon, a halogenated aromatic hydrocarbon or a halogenated alkyl substituted aromatic hydrocarbon.

13. A method for producing a m-halogenated ethylbenzene, comprising the steps of bringing the corresponding halogenated ethylbenzene into contact with an acidic zeolite containing at least one metal selected among the metals of Groups 7 to 11, for isomerization, and separating said m-halogenated ethylbenzene from the resulting halogenated ethylbenzene isomer mixture, by contacting it with an adsorbent containing a zeolite X containing an alkali metal and/or an alkaline earth metal or an adsorbent containing a zeolite Y containing sodium, and a desorbent.

* * * * *

UNITED STATES PATENT AND TRADEMARK OFFICE
CERTIFICATE OF CORRECTION

PATENT NO. : 6,235,952 B1
DATED : May 22, 2001
INVENTOR(S) : Minomiya et al.

It is certified that error appears in the above-identified patent and that said Letters Patent is hereby corrected as shown below:

Delete original specification (not claims), to be replaced with specification (not claims) as shown on the attached sheets.

Signed and Sealed this

Twenty-fourth Day of August, 2004

JON W. DUDAS
*Director of the United States Patent and Trademark Office*

US 6,235,952 B1

METHOD FOR ISOMERIZING HALOGENATED ETHYLBENZENE AND METHOD FOR SEPARATING HALOGENATED ETHYLBENZENE ISOMERS

TECHNICAL FIELD

The present invention relates to a method for isomerizing a halogenated ethylbenzene and a method for separating halogenated ethylbenzene isomers. In more detail, the present invention relates to a method for isomerizing a halogenated ethylbenzene by bringing the same into contact with an acidic zeolite, for obtaining a desired isomer, and relates particularly to a method for separating and recovering a m-halogenated ethylbenzene from a mixture of halogenated ethylbenzene isomers.

BACKGROUND ARTS

Halogenated ethylbenzenes are known as important intermediate products for preparation of agricultural chemicals, etc. Especially m-chloroethylbenzene (hereinafter chloroethylbenzene is abbreviated as CEB) or m-bromoethylbenzene (hereinafter bromoethylbenzene is abbreviated as BEB) is useful as a raw material for production of agricultural chemicals having specific bioactivity as an isomer that differs from the bioactivity of the p- and o-isomers. CEB or BEB is mainly produced by an aromatic ring chlorination or bromination reaction of ethylbenzene, but since the reaction is very strong in producing ortho-orientation and para-orientation, the m-isomer can be produced only in a small amount.

Therefore, CEB and BEB isomerization methods have an important technical significance. Conventionally known isomerization reactions for these compounds include a method using aluminum chloride, etc. as a catalyst as disclosed in Olah. G. A. J. Org. CHEM. 27,3464 (1962), a method using $HF-BF_3$ as a catalyst disclosed in Japanese Patent Laid-Open (Kokai) 46-11809, etc. Furthermore, Idar A. Acta Chemica Scandinavica B39,437 (1985) describes a chloroethy-lbenzene isomerization reaction using a mordenite-type zeolite. Furthermore, methods for isomerizing a halogenated toluene using a zeolite as a catalyst are disclosed in Japanese Patent Laid-Open (Kokai) Nos. 57-40428, 85330, 163327 and 7-309792.

However, in the isomerization of halogenated ethylbenzenes, it has been difficult to efficiently isomerize using conventional catalysts such as aluminum chloride and $HF-BF_3$ since a disproportionation reaction accompanying the de-ethylation reaction or intermolecular migration of ethyl groups is likely to occur, unlike the isomerization reactions of halogenated toluenes. Furthermore, because of such problems as the enormous amounts of catalyst needed for isomerization, corrosion of the reactor and environmental problems in the treatment of waste catalyst, the conventional methods are not efficient. The isomerization reaction using a mordenite catalyst is less serious among these problems, but has a disadvantage that since the catalyst life is short, the zeolite must be regenerated after hundreds of hours. So, a method for more efficiently obtaining a desired halogenated ethylbenzene is strongly demanded.

For separation of halogenated ethylbenzene isomers, since the halogenated ethylbenzene isomers are not very different in boiling points, a precision distillation column having a very large number of stages is necessary for separating them. So, it has been difficult to efficiently separate from the mixture a m-halogenated ethylbenzene of high purity.

As methods for separating the isomers of chlorotoluene, which are structurally different from the halogenated ethylbenzenes of the present invention. These include Japanese Patent Publication (Tokko) No.375155 which discloses an adsorption separation method using a zeolite X as the adsobent, and Japanese Patent Laid-Open (Kokai) Nos. 57-31627, 35528 and 91933 which disclose adsorption separation methods using a K ion exchanged zeolite Y as the adsorbent. These methods can separate the m-isomer from the p-isomer by adsorption, but cannot separate the m-isomer from the o-isomer, and m-chlorotoluene cannot be individually separated as an extract component or raffinate component. Furthermore, Japanese Patent Laid-Open (Kokai) Nos. 58-131923 and 59-176223 disclose m-chlorotoluene separation methods using an Ag and K ion exchanged zeolite Y or a Na and Cu ion exchanged zeolite Y as the adsorbent, and these methods can separate m-chlorotoluene as a raffinate component. However, as far as the inventors examined, these adsorbents could little separate m-CEB. As described so far, no method for both adsorbing and separating a halogenated ethylbenzene has been known at all, and there has been no idea of attempting it all.

DISCLOSURE OF THE INVENTION

The inventors studied intensively in order to solve the problem, and as a result, found that a halogenated ethylbenzene can be isomerized by bringing the same into contact with an acidic zeolite containing at least one metal selected from the metals of Groups 7 to 11. Thus, the present invention has been completed.

The present invention relates to a method of isomerizing a halogenated ethylbenzene, comprising the step of bringing the halogenated ethylbenzene into contact with an acidic zeolite containing at least one metal selected from the metals of Groups 7 to 11 for isomerizing it. In the present invention, it is preferable that the isomerization method is effected in the presence of hydrogen, and that the acidic zeolite is a faujasite-type, beta-type, mordenite-type or pentasil-type zeolite. Furthermore, it is preferable that the halogen of the halogenated ethylbenzene is chlorine or bromine.

On the other hand, the inventors studied intensively the method for efficiently separating a halogenated ethylbenzene, and found that m-isomer can be efficiently separated from a mixture of halogenated ethylbenzene isomers, particularly of isomers of CEB or BEB, by adsorption separation, using an adsorbent containing a specific zeolite and a desorbent. Thus, the present invention as a method for separating halogenated ethyl benzene isomers has been completed. The present invention further relates to a method for separating halogenated ethylbenzene isomers, comprising the step of separating a m-halogenated ethylbenzene from a mixture of halogenated ethylbenzene isomers by contacting said isomers with an adsorbent containing a zeolite X containing an alkali metal and/or alkaline earth metal, or an adsorbent containing a zeolite Y containing sodium, and a desorbent.

In the present invention, the following two separation embodiments are preferable: (a) separating halogenated ethylbenzene isomers, comprising the step of separating a m-halogenated ethylbenzene as an extract component using an adsorbent containing a zeolite X-containing alkali metal cations and not containing silver cations, or containing silver cations in an amount less than 10% of the ion exchange sites, or containing a zeolite Y containing sodium, and (b) a method for separating halogenated ethylbenzene isomers, comprising the step of separating a m-halogenated ethylbenzene as a raffinate component using an adsorbent containing a zeolite X containing alkali metal and/or alkaline earth metal cations and containing silver cations in an amount of 10% or more of the ion exchange sites.

The present invention is especially effective when the mixture of halogenated ethylbenzene isomers is a mixture of chloroethylbenzene isomers or a mixture of bromoethylbenzene isomers.

Furthermore, in the present invention, it is preferable that the desorbent used is an alkyl substituted aromatic hydrocarbon, a halogenated aromatic hydrocarbon or a halogenated alkyl substituted aromatic hydrocarbon.

BRIEF DESCRIPTION OF THE DRAWING

Figure 1:
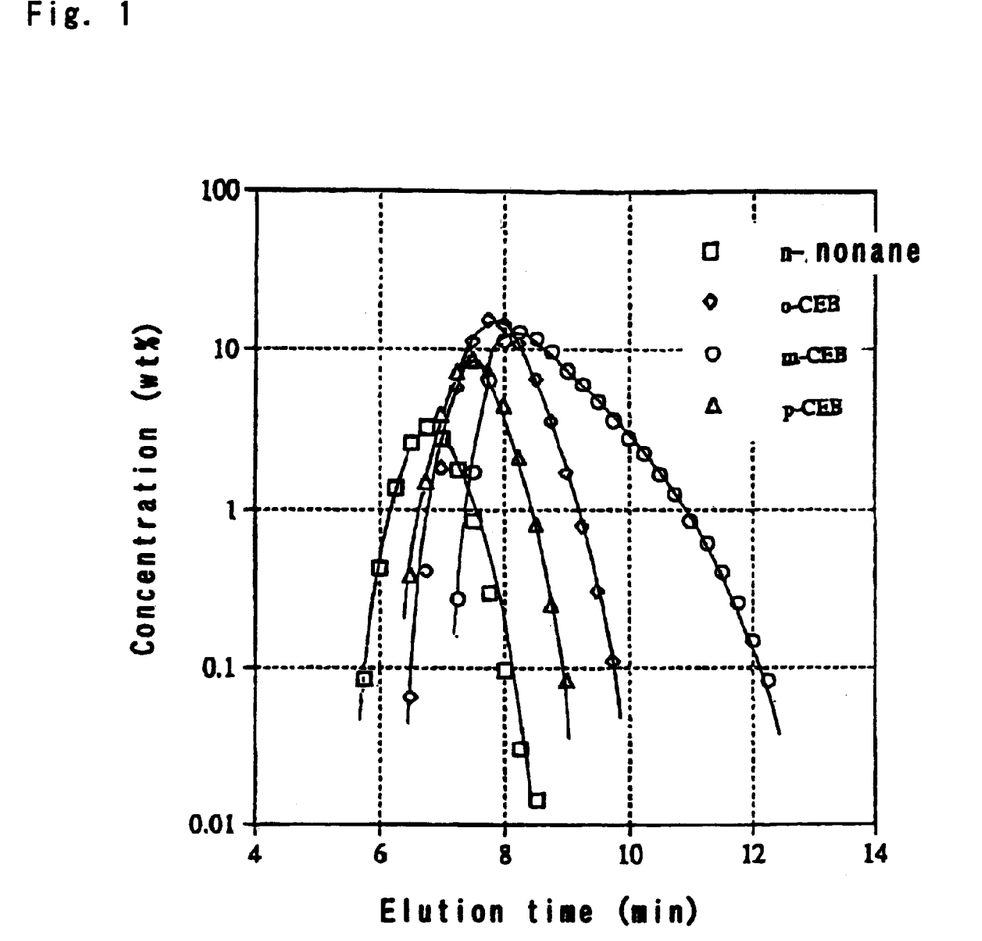
FIG. 1 is a diagram showing the amounts of the respective components eluted with the lapse of time in Example 30 of the present invention.

FIG. 1 is a diagram showing the amounts of the respective components eluted with the lapse of time in Example 30 of the present invention.

THE BEST EMBODIMENTS OF THE INVENTION

The zeolite used in the halogenated ethylbenzene isomerization method of the present invention can be an acidic zeolite, and it is preferable that the acidic zeolite is a faujasite-type, beta-type, mordenite-type or pentasil-type zeolite. A mordenite-type zeolite and a pentasil-type zeolite are more preferable. A method for synthesizing a faujasite-type zeolite is disclosed, for example, in Japanese Patent Publication (Tokko) No. 52-15400, etc. Methods for synthesizing a beta-type zeolite are disclosed, for example, in U.S. Pat. No. 3,308,069 and Japanese Patent Publication (Tokko) 7-223989. Methods for synthesizing a mordenite-type zeolite are disclosed, for example, in Japanese Patent Publication (Tokko) No. 47-46677, Japanese Patent Laid-Open (Kokai) No. 55-26529 and Japanese Patent Publication (Tokko) No. 3-31006. Methods for synthesizing a pentasil-type zeolite are disclosed, for example, in U.S. Pat. Nos. 3,702,886 and 4,511,547 and Japanese Patent Publication (Tokko) No. 60-35284.

When any of said zeolites is used for the isomerization method of the present invention, it is usually preferable to use the zeolite as a formed product, though not so limited. The forming method is not especially limited, and can be, for example, a rolling method, an extrusion method or a compression method, etc. For forming, if necessary, a binder such as alumina sol or clay, etc. can be added. The formed zeolite is usually calcined at 300 to 700° C., to be activated for use as a catalyst.

When any of the zeolites is used for the isomerization method of the present invention, it is used as an acidic zeolite. An acidic zeolite can be obtained, as is well known, by replacing the cations in a zeolite by hydrogen ions or divalent or higher valent cations. It is especially preferable that the cations are replaced by hydrogen ions, since the activity is high.

For replacing the cations in a zeolite by hydrogen ions, usually the zeolite is ion-exchanged directly by an acid aqueous solution, or the metal cations are ion-exchanged by ammonium ions, followed by burning. If the zeolite contains organic nitrogen-containing ions beforehand, the organic nitrogen-containing cations can be decomposed by burning for conversion into hydrogen ions, to obtain an acidic zeolite.

The halogenated ethylbenzene used in the method for isomerizing a halogenated ethylbenzene of the present invention can have the substituting halogen position at the ortho (o-), meta (m-) or para (p-) position to the ethyl group. It is preferable that the halogen is chlorine or bromine, and two or more halogens may also substitute. The raw material for isomerization of the present invention can be a single isomer or a mixture of isomers.

The halogenated ethylbenzenes which can be used include, for example, o-chloroethylbenzene, m-chloroethylbenzene, p-chloroethylbenzene, o-bromoethylbenzene, m-bromoethylbenzene, p-bromoethylbenzene, 1,3-dichloro-4-ethylbenzene, 1,3-dichloro-5-ethylbenzene, 1-chloro-2,4-diethylbenzene, 1-chloro-3,5-diethylbenzene, etc.

The isomerization reaction of the present invention can be effected by the flow method or the batch method. The reaction is effected with heating. The reaction temperature is usually 100 to 500° C., preferably 150 to 400° C. The reaction pressure is not especially limited, and can be set at atmospheric pressure to any desired pressure. The weight hourly space velocity (WHSV) as the raw material supply velocity per catalyst weight in the reaction is usually 0.01 to 50 hr$^{-1}$ preferably 0.1 to 10 hr$^{-1}$.

In the reaction of the present invention, a halogenated benzene and/or benzene can exist as a diluent together with the raw halogenated ethylbenzene. The dilution ratio is usually 1/20–20/1 (wt/wt), preferably 1/5–5/1 (wt/wt) as a ratio by weight to the halogenated ethylbenzene.

The reaction of the present invention is effected usually in the presence of hydrogen. The amount of hydrogen supplied is usually 0.01 to 40 mol %, preferably 1 to 25 mol % based on the amount of the halogenated ethylbenzene.

The isomerization catalyst of the present invention must contain at least one metal selected from the metals of Groups 7 to 11. The metals which can be used here include silver and copper of Group 11, rhenium of Group 7 and iron, nickel, platinum, etc. of Groups 8 to 10. Especially preferable is silver or rhenium. Methods for introducing the metal include the impregnation method, ion exchange method, kneading method, etc. The metal supply sources which can be used include hydrochlorides, nitrates, oxides, etc. The amount of the metal introduced is 0.01 wt % to 5.0 wt % as metal atoms based on the total amount of the catalyst in every case. A preferable range is 0.01 wt % to 1.0 wt %.

The presence of the diluent and hydrogen and the introduction of a metal into the catalyst are effective for preventing the loss of the halogenated ethylbenzene by side reactions such as disproportionation reactions and the degradation of catalyst activity.

The method for separating halogenated ethylbenzene isomers of the present invention is described below in detail.

The zeolite X or Y used in the method for separating halogenated ethylbenzene isomers of the present invention is a faujasite-type zeolite which is a crystalline aluminosilicate represented by the following formula:

where M stands for cations, and n stands for their valence. In a faujasite-type zeolite, x is usually in a range of 2 to 6. The faujasite-type zeolite can be classified into a zeolite X with 2 to 3 as x, and a zeolite Y with 3 to 6 as x. y depends on the hydration degree.

In the present invention, a specific zeolite X or a specific zeolite Y can be used. That is, a zeolite X containing an alkali metal and/or alkaline earth metal as cations M or a zeolite Y containing sodium as cations M is used.

The faujasite-type zeolite is usually obtained as a zeolite containing sodium as cations M, and the cations can be replaced by various cations by ion exchange. The cation exchange is usually effected by bringing the zeolite into contact with an aqueous solution of a compound containing the intended cations such as a hydrochloride, nitrate, sulfate, carbonate or hydroxide, etc. The ion exchanged amount can be set as desired by the concentration of the aqueous solution, though depending on the kind of cations. After completion of ion exchange, the zeolite is sufficiently rinsed, to remove the sodium ions, chlorine ions, nitrate ions, etc. dissolved in the aqueous solution due to ion exchange.

When a m-halogenated ethylbenzene is separated as an extract component in the present invention, a zeolite X containing alkali metal cations and not containing silver cations or containing silver cations in an amount less than 10% of the ion exchange sites, and a zeolite Y containing sodium ions are preferable. The alkali metal cations of the zeolite X include Li, Na, K, Cs, etc., and sodium is especially preferable.

When a m-halogenated ethylbenzene is separated as a raffinate component in the present invention, a zeolite X containing alkali metal and/or alkaline earth metal cations and containing silver cations by 10% or more of the ion exchange sites can be preferably used. The alkali metals include Li, Na, K, Cs, etc., and the alkaline earth metals include Mg, Ca, Sr, Ba, etc.

Especially preferable combinations are Ag and Ba, Ag and K, etc. Such a zeolite can be obtained by ion-exchanging the sodium of a faujasite-type zeolite by an alkali metal or alkaline earth metal, and then ion-exchanging 10% to 70% of the sodium cation sites of the zeolite by silver. It is preferable to exchange 10% to 40%. When silver cations are not present or contained in an amount less than 10%, the m-halogenated ethylbenzene can be separated as an extract component.

The adsorbent can be a solidified zeolite only or can be in the form of grains obtained by granulating a zeolite together with a binder such as alumina or clay.

Before the adsobent is used, the crystal water in the zeolite is removed beforehand. Usually, by heating at 200 to 600° C., most of crystal water can be removed.

The adsorption separation technique for adsorbing and separating the CEB isomer mixture or BEB isomer mixture using the adsorbent of the present invention can be the so-called chromatographic fractionation method or an adsorption separation method using a simulated moving bed as a continuous version of said method.

The continuous adsorption separation technique using a pseudo-moving bed is effected by continuously using the following adsorption operation, concentration operation and desorption operation in circulation.

[1] Adsorption operation: The raw materials containing a halogenated ethylbenzene isomer mixture are brought into contact with the adsorbent of the present invention, and the most adsorbable component is selectively adsorbed. The most adsorbable component is recovered with the desorbent described later, as an extract component.

[2] Concentration operation: The raffinate containing a less adsorbable component in a large amount is further brought into contact with the adsorbent, and the most adsorbable component is selectively adsorbed, while the less adsorbable component in the raffinate becomes highly purified.

[3] Desorption operation: The highly purified less adsorbable component is recovered as a raffinate. On the other hand, the most adsorbable component is expelled from the adsorbent by a desorbent, and recovered as an extract component together with the desorbent.

It is preferable that the desorbent used for the above adsorption separation method is an alkyl substituted aromatic hydrocarbon or a halogenated aromatic or halogenated alkyl substituted aromatic hydrocarbon. The alkyl substituted aromatic hydrocarbons which can be used as desorbents include, for example, toluene, ethylbenzene, xylene, propylbenzene, trimethylbenzene, diethylbenzene, tetramethylbenzene, etc.

The halogenated aromatic hydrocarbons which can be used as desorbents include, for example, chlorobenzene, dichlorobenzene, trichlorobenzene, etc. The halogenated alkyl substituted aromatic hydrocarbons include, for example, chlorotoluene, dichlorotoluene, chloroxylene, etc.

Especially for separation of m-CEB, preferable desorbents are p-xylene, 1,2,4-trimethylbenzene, m-chlorotoluene and 3,4-dichlorotoluene. For separation of m-BEB, preferable desorbents are p-xylene and 3,4-dichloratoluene. Any or more as a mixture of these adsorbents can be used.

As operation conditions of the adsorption separation method, the temperature is usually room temperature to 350° C., preferably 50 to 250° C., and the pressure is usually atmospheric pressure to 4 MPa, preferably atmospheric pressure to 3 MPa. The adsorption separation method of the present invention can be effected also in vapor phase, but to decrease the unpreferable side reactions of the raw materials and desorbent by lowering the operation temperature, it is preferable to execute the method in the liquid phase.

EXAMPLES

The present invention will be described below in more detail with reference to examples and comparative examples, which are not intended to restrict the scope of the invention.

The synthesis of zeolites, preparation of isomerizing catalysts, adsorption characteristics of adsorbents and preparation of adsorbents respectively used in the following examples and comparative examples are described below.

[Synthesis of Zeolites]

Zeolite 1

A resin beaker was charged with 229.3 g of ion exchange water, and 3.1 g of sodium hydroxide and 14.7 g of sodium aluminate ($Al_2O_3$=18.76 wt %, $Na_2O$=19.71 wt %, $H_2O$=61.53 wt %) were added. The mixture was sufficiently stirred for dissolution. Then, 9.2 g of tartaric acid was added, and the mixture was sufficiently stirred. Furthermore, 48 g of silicic acid powder ($SiO_2$ 89.33 wt %, $Na_2O$=0.31 wt %, $Al_2O_3$ 0.34 wt %, $H_2O$=10.02 wt %) was added, to prepare a slurry. The slurry was supplied into a 500 cc stainless steel autoclave and reaction was effected with sufficient stirring at 160° C. for 3 days, to produce a zeolite. The zeolite was sufficiently washed by distilled water, and dried at 120° C. overnight, to obtain a pentasil-type zeolite with a $SiO_2$/$Al_2O_3$ molar ratio of 20.

Zeolite 2

A resin beaker was charged with 228.5 g of ion exchange water, and 5.4 g of sodium hydroxide and 35.9 g of sodium aluminate ($Al_2O_3$=18.76 wt %, $Na_2O$=19.71 wt %, $H_2O$=61.53 wt % were added. The mixture was sufficiently stirred for dissolution. Then, 12.5 g of tartaric acid was added, and the mixture was sufficiently stirred. Furthermore, 45.9 g of silicic acid powder ($SiO_2$=89.33 wt %, $Na_2O$=0.31 wt %, $Al_2O_3$ 0.34 wt %, $H_2O$=10.02 wt %) was added, to prepare a slurry. The slurry was supplied into a 500 cc stainless steel autoclave, and reaction was effected with sufficient stirring at 165° C. for 2 days, to produce a zeolite. The zeolite was sufficiently washed with distilled water and dried at 120° C. overnight, to obtain a mordenite-type zeolite with a $SiO_2/Al_2O_3$ molar ratio of 10.

Zeolite 3

A resin beaker was charged with 220.3 g of ion exchange water, and 19.6 g of sodium hydroxide and 11.3 g of sodium aluminate ($Al_2O_3$=18.76 wt %, $Na_2O$=19.71 wt %, $H_2O$=61.53 wt %) were added. The mixture was sufficiently stirred for dissolution. Then, 9.1 g of tartaric acid was added, and the mixture was sufficiently stirred. Furthermore, 46.3 g of silicic acid powder ($SiO_2$=89.33 wt %, $Na_2O$=0.31 wt %, $Al_2O_3$ 0.34 wt %, $H_2O$=10.02 wt %) was added, to prepare a slurry. The slurry was supplied into a 500 cc stainless steel autoclave, and reaction was effected with stirring at 155° C. for 2 days, to produce a zeolite. The zeolite was sufficiently washed with distilled water and dried at 120° C. overnight, to obtain a mordenite-type zeolite with a $SiO_2/Al_2O_3$ molar ratio of 20.

Zeolite 4

A resin beaker was charged with 232.6 g of ion exchange water, and 0.67 g of sodium hydroxide was added for sufficient dissolution. Then, 26.9 g of tetraethylammonium hydroxide (content 20 wt %, $H_2O$=80 wt %) was added, and in succession, 10.2 g of sodium aluminate ($Al_2O_3$=18.76 wt %, $Na_2O$=19.71 wt %, $H_2O$=61.53 wt %) was added. The mixture was sufficiently stirred, and finally 33 g of silicic acid powder($SiO_2$=89.33 wt %, $Na_2O$=0.31 wt %, $Al_2O_3$=0.34 wt %, $H_2O$=10.02 wt %) was added, to prepare a slurry. The slurry was supplied into a 500 cc stainless steel autoclave, and reaction was effected with sufficient stirring at 160° C. for 7 days, to produce a zeolite. The zeolite was sufficiently washed with distilled water and dried at 120° C. overnight, to obtain a mordenite-type zeolite with a $SiO_2/Al_2O_3$ molar ratio of 20.

[Preparation of Catalysts]

Catalyst 1

Alumina sol ($Al_2O_3$=10 wt %) was added by 15 parts by weight as alumina to 100 parts by weight of the zeolite 1, and the mixture was formed, dried at 120° C. overnight and calcined at 500° C. for 2 hours. The formed zeolite was ion-treated using 10 wt % ammonium chloride aqueous solution (solid liquid ratio 2.0 l/kg) at 85° C. for 1 hour five times, sufficiently washed with distilled water, dried at 120° C. overnight and calcined at 550° C. for 2 hours in air, to obtain an acidic pentasil-type zeolite catalyst.

Catalyst 2

An acidic mordenite-type zeolite catalyst was obtained as described to obtain the catalyst 1, except that the zeolite 2 was used and that calcination was effected at 520° C. for 2 hours in air.

Catalyst 3

An acidic mordenite-type zeolite catalyst was obtained as described to obtain the catalyst 1, except that the zeolite 3 was used and that calcination was effect ed at 520° C. for 2 hours in air.

Catalyst 4

Alumina sol ($Al_2O_3$=10 wt %) was added by 15 parts by weight as alumina to 100 parts by weight of the zeolite 4, and the mixture was formed, dried at 120° C. overnight and calcined at 500° C. for 2 hours. The formed zeolite was ion-treated using 10 wt % ammonium chloride aqueous solution (solid liquid ratio 2.0 l/kg) at 85° C. for 1 hour five times and sufficiently washed with distilled water. The formed zeolite was immersed in a rhenium peroxide ($Re_2O_7$) aqueous solution with a solid liquid ratio of 2.0 l/kg adjusted to be 0.1 wt % as rhenium metal content, at room temperature for 4 hours, filtered, dried at 120° C. overnight, and calcined at 550° C. for 2 hours in air, to obtain a rhenium carried acidic mordenite-type zeolite catalyst.

Catalyst 5

Alumina sol ($Al_2O_3$=10 wt %) was added by 15 parts by weight as alumina to 100 parts by weight of the zeolite 4, and the mixture was formed, dried at 120° C. overnight and calcined at 500° C. for 2 hours. The formed zeolite was ion-treated using 10 wt % ammonium chloride aqueous solution (solid liquid ratio 2.0 l/kg) at 85° C. for 1 hour five times, sufficiently washed with distilled water, dried at 120° C. overnight and calcined at 550° C. for 2 hours in air to obtain an acidic mordenite-type zeolite.

[Adsorption characteristics of adsorbents]

In the examples, the adsorption characteristic of an adsorbent was expressed by the adsorption selectivity ($\alpha$) of the following formula (1):

$$\alpha(o/m \text{ or } p/m) = \frac{\left[\dfrac{\text{weight percent of } o \text{ or } p}{\text{weight percent of } m}\right]_A}{\left[\dfrac{\text{weight percent of } o \text{ or } p}{\text{weight percent of } m}\right]_U} \quad (1)$$

where o, m or p stands for o-, m- or p-halogenated ethylbenzene respectively; A stands for adsorption phase; and U stands for liquid phase balanced with adsorption phase.

If the $\alpha$ value in the above formula is larger than 1, the m-halogenated ethylbenzene is less likely to be adsorbed than the o- and p-halogenated ethylbenzenes, and if smaller than 1, the m-halogenated ethylbenzene is more likely to be adsorbed than the o- and p-halogenated ethylbenzenes. The adsorbent suitable for separating and recovering the m-halogenated ethylbenzene is preferably larger than 1 or smaller than 1, being close to 0 in both $\alpha$ (o/m) and $\alpha$ (p/m).

[Preparation of adsorbents]

The adsorbents 1 to 5 used in the examples were prepared according to the following methods:

Adsorbent 1

Alumina sol (Nissan Chemical No. 200:$Al_2O_3$ 10 wt %) as a binder was added by 15 parts by weight as alumina to 100 parts by weight a sodium type zeolite X (hereinafter expressed as NaX) (Zeolam F-9 powder produced by Tosoh Corp.), and the mixture was granulated to 0.15–0.5 mm dia., to obtain a NaX type zeolite. It was dried at 120° C. and calcined at 500° C.

Adsorbent 2

Alumina sol (Nissan Chemical No. 200:$Al_2O_3$=10 wt %) as a binder was added by 15 parts by weight as alumina to 100 parts by weight of a sodium type zeolite Y (hereinafter expressed as NaY) (Zeolam Na-5.1Y powder produced by Tosoh Corp.), and the mixture was granulated to 0.15–0.5 mm dia., to obtain a NaY type zeolite. It was dried at 120° C. and calcined at 500° C.

Adsorbent 3; Ag—BaX

The adsorbent 1 was treated for ion exchange using 10 wt % barium nitrate aqueous solution (solid liquid ratio 3.0 l/kg) at 85° C. for 1 hour six times and sufficiently washed with distilled water. Then, using a silver nitrate aqueous solution (solid liquid ratio 3.0 l/kg) as silver corresponding to 40% of the Na cation sites of NaX, it was allowed to stand at room temperature for 30 minutes and treated for ion exchange at 85° C. for 1 hour, sufficiently washed with distilled water, dried at 120° C. and calcined at 500° C.

Adsorbent 4: Ag—NaX

Using a silver nitrate aqueous solution (solid liquid ratio 3.0 l/kg) as silver corresponding to 5% of the Na cation sites of NaX, the adsorbent 1 was allowed to stand at room temperature for 30 minutes and treated for ion exchange at 85° C. for 1 hour, sufficiently washed with distilled water, dried at 120° C. and calcined at 500° C.

Adsorbent 5: Ag—KY

Using 10 wt % potassium nitrate aqueous solution (solid liquid ratio 3.0 l/kg), the adsorbent 2 was treated for ion exchange at 85° C. for 1 hour ten times, and sufficiently washed with distilled water. Then, using a silver nitrate aqueous solution (solid liquid ratio 3.0 l/kg) as silver corresponding to 30% of the Na cation sites of NaY, it was allowed to stand at room temperature for 30 minutes and treated for ion exchange at 85° C. for 1 hour, sufficiently washed with distilled water, dried at 120° C. and calcined at 500° C. [Isomerization reaction]: Examples and comparative examples of isomerization reaction are described below.

Example 1

A 10 ml stainless steel autoclave was charged with 2 g of a CEB isomer mixture (o-:m-:p-=49.2:2.7:48.1 (wt %)), and 1.0 g of the catalyst 4 was added. At room temperature and atmospheric pressure, 20 ml of hydrogen was supplied, and reaction was effected at 270° C. for 2 hours. The amount of hydrogen supplied corresponded to 5.6 mol % of the CEB isomer mixture. After completion of reaction, the reaction product was analyzed by gas chromatography. The results are shown in Table 1.

Example 2

Reaction was effected as described in Example 1, except that 2.5 g of a mixture consisting of the CEB isomer mixture used in Example 1 and CB (CEB/CB=4 (wt/wt)) was used. The results are shown in Table 1.

Example 3

Reaction was effected as described in Example 1, except that 3 g of a mixture consisting of the CEB isomer mixture used in Example 1 and CB (CEB/CB=2 (wt/wt)) was used. The results are shown in Table 1.

TABLE 1

| Example | Raw Material | CEB composition, % | | |
|---|---|---|---|---|
| | | o- | m- | p- |
| 1 | CEB | 29.8 | 49.4 | 20.7 |
| 2 | CEB/CB = 4 | 31.5 | 47.2 | 21.3 |
| 3 | CEB/CB = 2 | 32.6 | 45.8 | 21.6 |

Example 4

Reaction was effected using a fixed bed flow reactor and a CEB isomer mixture (o-:m-:p-=59.0:5.6:35.4 (wt %)), except that the catalyst 4 was used. The results are shown Table 2.

Example 5

Reaction was effected, except that the catalyst 4 was used and that a mixture consisting of a CEB isomer mixture (o-:m-:p-=59.0:5.6:35.4 (wt %)) and CB (CED/CB=2 (wt/wt)) was used. The results are shown in Table 2.

Comparative Example 1

Reaction was effected as described in Example 4, except that the catalyst 5 was used. The results are shown in Table 2. It can be seen that an acidic mordenite-type zeolite catalyst without containing any metal declines very greatly in catalyst activity even if hydrogen exists.

TABLE 2

| | m-CEB composition, % Reaction time, hr | | | CEB recovery rate, % with m-CEB/CEB = |
|---|---|---|---|---|
| Example | 10 | 100 | 200 | 48 wt % |
| 13 | 48.7 | 48.5 | 48.2 | 97.0 |
| 14 | 50.1 | 49.7 | 49.4 | 99.0 |
| 1 | 50.3 | 45.3 | 43.1 | 96.0 |

Reaction conditions: WHSV (CEB) 1.3 $hr^{-1}$, reaction temperature 245° C., reaction pressure 4 MPa [Adsorption separation]: Examples and comparative examples of adsorption separation are described below.

Example 6–Example 13

The adsorption selectivities between respective CEB isomers were measured using the adsorbent 1 and various desorbents.

For measurement, a 5 ml autoclave was charged with 3 g of a liquid phase mixture and 1.5 g of the adsorbent calcined at 500° C., and the mixture was allowed to stand at 130° C. for 1 hour with stirring sometimes. The composition of the supplied liquid phase mixture was n-nonane:desorbent:CEB (o:m:p=37%:44%:19%)=8%:60%:32%. The n-nonane was added as an internal standard substance for gas chromatography, which was substantially inactive in adsorption under the above experimental conditions.

The composition of the liquid phase mixture after contact with the adsorbent was analyzed by gas chromatography, and adsorption selectivities between respective CEB isomers were obtained using the formula (1). The results are shown in Table 6.

TABLE 3

| Example | Desorbent | $\alpha p/m$ | $\alpha o/m$ |
|---|---|---|---|
| 6 | p-xylene | 0.21 | 0.46 |
| 7 | iso-propylbenzene | 0.41 | 0.71 |
| 8 | 1,2,4-trimethylbenzene | 0.43 | 0.46 |
| 9 | 1,2,3,5-tetramethylbenzene | 0.48 | 0.78 |
| 10 | o-chlorotoluene | 0.39 | 0.76 |
| 11 | 3,4-dichlorotoluene | 0.48 | 0.78 |
| 12 | 1,2,4-trichlorobenzene | 0.40 | 0.79 |

Example 13 and Example 14

Experiments were performed as described in Example 15, except that the adsorbent 2 was used. In Example 13, o-xylene was used as the desorbent, and in Example 14, 1,2,4-trimethylbenzene was used as the desorbent. The results are shown in Table 4.

TABLE 4

| Example | Desorbent | $\alpha p/m$ | $\alpha o/m$ |
|---|---|---|---|
| 13 | o-xylene | 0.20 | 0.54 |
| 14 | 1,2,4-trimethylbenzene | 0.30 | 0.54 |

Example 15–Example 17

Experiments were performed as described in Example 6, except that the adsorbent 3 was used. In Example 15, o-xylene was used as the desorbent, and in Example 16, m-chlorotoluene was used as the desorbent. In Example 17, 3,4-dichlorotoluene was used as the desorbent. The results are shown in Table 5.

TABLE 5

| Example | Desorbent | αp/m | αo/m |
|---|---|---|---|
| 15 | o-xylene | 1.38 | 1.28 |
| 16 | m-chlorotoluene | 2.54 | 1.71 |
| 17 | 3,4-dichlorotoluene | 2.08 | 1.29 |

Example 18

An experiment was performed as described in Example 6, except that the adsorbent 4 was used and that 3,4-dichlorotoluene was used as the desorbent. The results are shown in Table 6.

TABLE 6

| Example | Desorbent | αp/m | αo/m |
|---|---|---|---|
| 4 | 3,4-dichlorotoluene | 0.45 | 0.88 |

Example 19

The adsorption selectivities between respective BEB isomers were measured using the adsorbent 1. The measuring method was as described in Example 6. The composition of the supplied liquid phase mixture was n-nonane desorbent:BEB (o:m:p=34%:40%:26%)=13%:46%:41%. The results are shown in Table 7.

TABLE 7

| Example | Desorbent | αp/m | αo/m |
|---|---|---|---|
| 19 | p-xylene | 0.24 | 0.44 |

Example 20

Adsorption selectivities between respective BEB isomers were measured using the adsorbent 3, as described in Example 6. As the desorbent, 3,4-dichlorotoluene was used. The composition of the supplied liquid phase mixture was n-nonane:desorbent:BEB (o:m:p=34%:40%:26%)= 13%:46%:41%. The results are shown in Table 8.

TABLE 8

| Example | Desorbent | αp/m | αo/m |
|---|---|---|---|
| 20 | 3,4-dichlorotoluene | 2.23 | 1.13 |

Comparative Example 2

An experiment was performed as described in Example 6, except that the adsorbent 1 was used and that xylene was used as the desorbent. The adsorption characteristics of chlorotoluene and CEB were compared, and the results are shown in Table 9.

TABLE 9

(Comparative Example)

| Desorbent | Chlorotoluene | | CEB | |
| | αp/m | αo/m | αp/m | αo/m |
|---|---|---|---|---|
| p-xylene | 0.68 | 0.97 | 0.21 | 0.46 |

Comparative Example 3

An experiment was performed as described in Example 6, except that the adsorbent 5 was used and that 3,4-dichlorotoluene was used as the desorbent. The adsorption characteristics of chlorotoluene and CEB were compared, and the results are shown in Table 10.

TABLE 10

(Comparative Example)

| Desorbent | Chlorotoluene | | CEB | |
| | αp/m | αo/m | αp/m | αo/m |
|---|---|---|---|---|
| 3,4-dichloratoluene | 1.41 | 1.40 | 1.68 | 1.09 |

Example 21

A 1 m long 4.75 mm inner dia. stainless steel column was packed with the adsorbent 1, and p-xylene as a desorbent was fed at a flow rate of about 1.8 ml/min in a 130° C. oil bath. While para-xylene was fed, about 1.6 ml of an isomer mixture consisting of CEB (o:m:p=37%:44%:19%):n-nonane=4:1 (ratio by weight) was introduced into the inlet of the column, as a raw material to be separated. The n-nonane was used as a reference for elution time, and its adsorption is virtually negligible compared with other components. The eluate from the outlet of the column was analyzed by gas chromatography, and elution curves shown in FIG. I were obtained.

Industrial Applicability

As described above, according to the present invention, a halogenated ethylbenzene can be isomerized by bringing the same into contact with a zeolite, for effectively obtaining a desired halogenated ethylbenzene. Furthermore, according to the present invention, by an adsorption separation method using a specific zeolite X or Y as the adsorbent, a m-halogenated ethylbenzene can be efficiently obtained from a mixture of halogenated ethylbenzene isomers. Therefore, the present invention is suitable for industrial production of a desired halogenated ethylbenzene, above all, a m-halogenated ethylbenzene.

What is claimed is:

1. A method for isomerizing a halogenated ethylbenzene, comprising the step of bringing said halogenated ethylbenzene into contact with an acidic zeolite containing at least one metal selected from the group consisting of metals of any of Groups 7 to 11, for isomerization.

2. A method for isomerizing a halogenated ethylbenzene, according to claim 1, wherein said isomerization is effected in the presence of hydrogen.

3. A method for isomerizing a halogenated ethylbenzene, according to claim 2, wherein said halogen is chlorine and/or bromine.

4. A method for isomerizing a halogenated ethylbenzene, according to claim 1, wherein said acidic zeolite is selected from the group consisting of faujasite, beta, mordenite and pentasil zeolite.

5. A method for isomerizing a halogenated ethylbenzene, according to claim 1, wherein said contact of said halogenated ethylbenzene with said acidic zeolite, is performed in the presence of a halogenated benzene and/or benzene.

6. A method for isomerizing a halogenated ethylbenzene, according to claim 1, wherein said isomerization reaction is conducted at a temperature of 150 to 400° C.

7. A method for separating a halogenated ethylbenzene isomer, comprising the step of separating a m-halogenated ethylbenzene from a mixture of halogenated ethylbenzenes, by contacting said mixture with an adsorbent containing a zeolite X containing an alkali metal and/or alkaline earth metal, or an adsorbent containing a zeolite Y containing sodium, and a desorbent.

8. A method for separating a halogenated ethylbenzene isomer, according to claim 7, wherein said halogen is chlorine and/or bromine.

9. A method for separating a halogenated ethylbenzene isomer, according to claim 7, wherein an adsorbent containing a zeolite X containing alkali metal cations and free of silver cations or containing silver cations in an amount less than 10% of the ion exchange sites, or an adsorbent containing a zeolite Y containing sodium as the adsorbent, to separate the m-halogenated ethylbenzene as an extract component.

10. A method for separating a halogenated ethylbenzene isomer, according to claim 7, wherein said mixture is contacted with an adsorbent containing a zeolite X containing alkali metal and/or alkaline earth metal cations and containing silver cations in an amount of 10% or more of the ion exchange sites, for separating the m-halogenated ethylbenzene as a raffinate component.

11. A method for separating a halogenated ethylbenzene isomer, according to claim 7, wherein said halogenated ethylbenzene isomer mixture is a chloroethylbenzene isomer mixture.

12. A method for separating a halogenated ethylbenzene isomer, according to claim 7, wherein said desorbent is an alkyl substituted aromatic hydrocarbon, a halogenated aromatic hydrocarbon or halogenated alkyl substituted aromatic hydrocarbon.

13. A method for producing a m-halogenated ethylbenzene, comprising the steps of bringing the corresponding halogenated ethylbenzene into contact with an acidic zeolite containing at least one metal selected among the metals of Groups 7 to 11, for isomerization, and separating said m-halogenated ethylbenzene from the resulting halogenated ethylbenzene isomer mixture, by contacting it with an adsorbent containing a zeolite X containing an alkali metal and/or an alkaline earth metal or an adsorbent containing a zeolite Y containing sodium, and a desorbent.

* * * * *